United States Patent [19]

Spademan

[11] Patent Number: 4,649,906

[45] Date of Patent: Mar. 17, 1987

[54] CUFF DEVICE

[76] Inventor: Richard G. Spademan, Box 6410, Incline Village, Nev. 89450

[21] Appl. No.: 687,251

[22] Filed: Dec. 28, 1984

Related U.S. Application Data

[63] Continuation-in-part of Ser. No. 601,924, Jun. 15, 1984, abandoned.

[51] Int. Cl.$^4$ .......................... A61F 5/04; A61F 2/78; A61F 5/01
[52] U.S. Cl. .................... 128/80 C; 128/88; 128/80 F; 623/32
[58] Field of Search ............... 128/80 C, 80 F, 88, 128/80 G; 3/22; 623/32, 40, 39, 50, 51

[56] References Cited

U.S. PATENT DOCUMENTS

| | | | |
|---|---|---|---|
| 73,768 | 1/1868 | Allen | 128/88 |
| 1,601,659 | 9/1926 | Von Harlingen | 128/80 C |
| 2,195,024 | 7/1938 | Bullock | 128/88 |
| 2,558,986 | 9/1947 | Seelert | 128/80 F |
| 4,088,130 | 5/1978 | Applegate | 3/22 |
| 4,220,148 | 9/1980 | Lehneis | 128/80 C |
| 4,320,747 | 3/1982 | Daniell, Jr. | 3/22 |
| 4,340,041 | 7/1982 | Frank | 128/80 C |
| 4,361,142 | 11/1982 | Lewis et al. | 128/80 C |
| 4,506,661 | 3/1985 | Foster | 128/88 |

Primary Examiner—Charles A. Pearson
Assistant Examiner—Tonya Eckstine
Attorney, Agent, or Firm—Townsend and Townsend

[57] ABSTRACT

A support including cuff components for engaging body parts articulated to each other about a joint, arms attached to and extending from the cuff components and pivotably attached to each other remote from the cuff components and in substantial alignment with the joint, and tightening cables attached to the cuff components and arms for temporarily increasing the tightness with which the cuff components engage the body parts in response to movement of one body part relative to the other body part.

32 Claims, 7 Drawing Figures

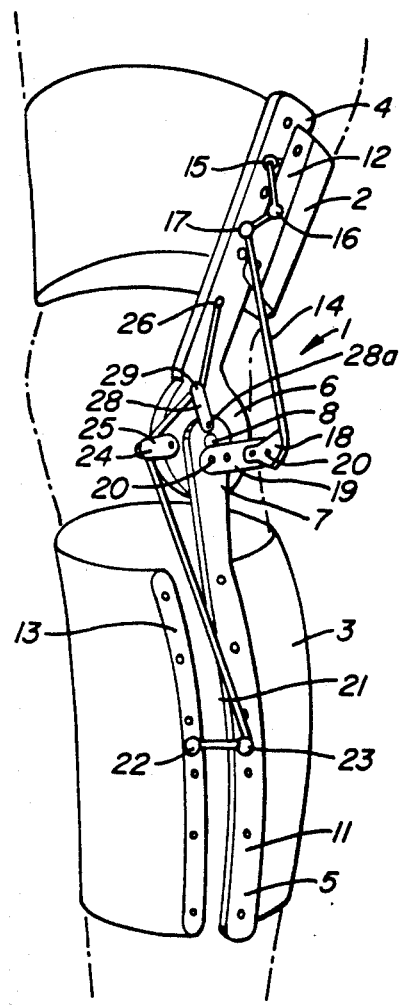
FIG._1.
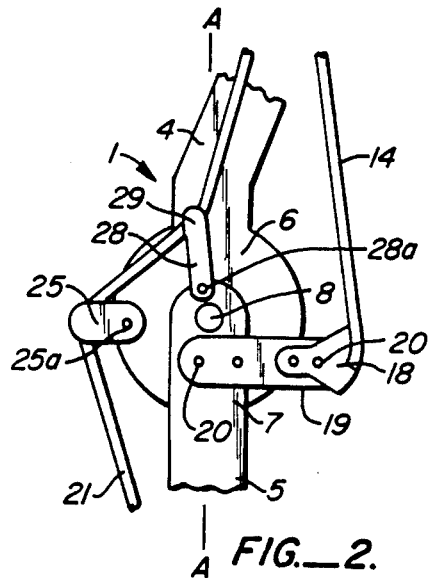
FIG._2.
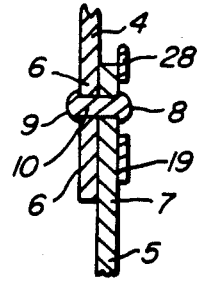
FIG._3.
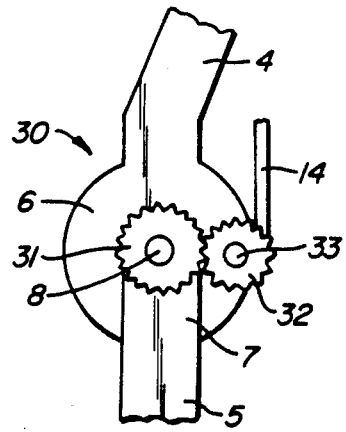
FIG._4.

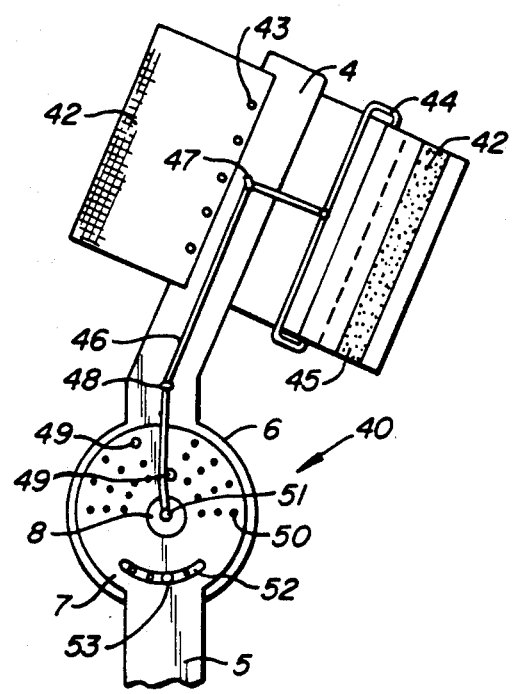
FIG._5.
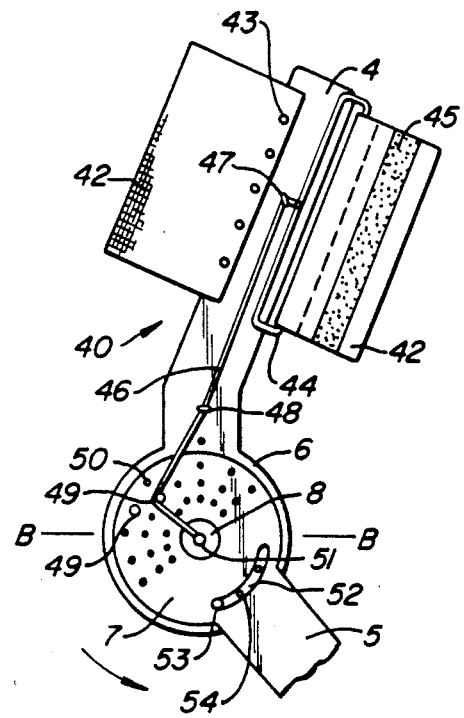
FIG._6.
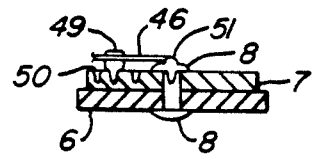
FIG._7.

CUFF DEVICE

RELATED APPLICATIONS

The present application is a continuation-in-part of applicant's application Ser. No. 601,924 filed June 15, 1984 now abandoned entitled Cuff Device.

BACKGROUND OF THE INVENTION

The present invention relates to therapeutic and prophylactic devices, particularly to a cuff device that dynamically tightens and loosens on a wearer's body part as another body part is moved.

Various compressive cuff devices are known such as the straps that hold braces on a patient's limb and trunk to protect ligaments, tendons and bones as they heal following injury or surgery. Various strapping devices are also used to help prevent injury or provide support for the chronic instability of a body part. Elastic stockings and inflatable cuffs are used to reduce edema and blood stasis in the extremities that result from disease, injury, prolonged confinement or surgery.

Unfortunately, at the present time, ideal conditions for the efficient application of these braces, cuffs and stockings cannot be achieved with conventional means. These supporting structures tend to be either too loose on the body part, in which case the support members cannot adequately stabilize the body part against undesirable or abnormal movement or fluid stasis or, more frequently, these supporting structures are held too tightly, intensifying discomfort. prolonging immobility and aggravating the problem of stasis or atrophy.

SUMMARY OF THE INVENTION

It is accordingly a primary object of the present invention to provide a cuff device that overcomes the drawbacks of previously known devices of the above known type.

Another object of the present invention is to provide a dynamic cuff assembly that momentarily tightens on a body part in response to movement of another body part.

It is still another object of the present invention to provide a dynamic cuff assembly that momentarily tightens and loosens from a close fit position on a body part in response to movement of another body part in desirable directions but not in other directions.

It is still another object of the present invention to provide a dynamic cuff assembly that can be adjusted to control the rate and amount of tightening and loosening of the cuff assembly on a body part in response to a predetermined movement in a predetermined direction from a predetermined position of another body part.

BRIEF DESCRIPTION OF THE DRAWINGS

In the drawings:

FIG. 1 is a perspective view of a cuff assembly of the present invention in extension showing the various parts.

FIG. 2 is an enlarged fragmentary side elevation view of the cuff assembly showing the pivot, lever and cam assembly.

FIG. 3 is a vertical sectional view taken along line A—A of FIG. 2.

FIG. 4 is an enlarged fragmentary side elevation view of the cuff assembly of an alternative embodiment of the present invention showing the pivot and gear assembly.

FIG. 5 is an enlarged fragmentary side elevation view of the cuff assembly of another alternative embodiment of the present invention showing the pivot and plate assembly in the normal position.

FIG. 6 is an enlarged fragmentary side elevation view of the cuff assembly of FIG. 5 pivoted from the normal position.

FIG. 7 is a vertical sectional view taken along line B—B of FIG. 6.

DESCRIPTION OF THE PREFERRED EMBODIMENTS

Referring to FIGS. 1-3, a cuff device for the lower extremity is shown, but it is understood that the principals of the invention are also applicable to other articulated body parts. There is shown in FIG. 1 a cuff assembly 1 which includes an upper limb engaging cuff component 2 and a lower limb engaging cuff component 3. These cuff components comprise a fitting means and are respectively adapted to engage the body parts above and below the articulation. A pair of arms 4 and 5 are respectively attached to and extend toward each other from the limb engaging components 2 and 3. These arms 4 and 5 terminate in movable overlaping end regions 6 and 7 remote from the fitting means and formed with aligned openings through which a single pivot pin 8 extends. A more complex slidable and pivotable orthotic joint can be used and additional arms can be located on the limbs. The pivot pin 8 has a head 9 and a section 10 secured in the opening in the end region 6 by a hexigonal shaped configuration complimentary to a hexigonal shaped opening in end region 6. End region 7 pivots freely about pivot pin 8. Thus, pivot pin 8 forms a pivot axis which is substantially perpendicular to the arms 4 and 5 and which coincides with the predominent axis to which swinging of the upper and lower limbs are limited. The arms 4 and 5 may be of a slightly flexible material construction such as metal or plastic. The cuff components 2 and 3 are fixed at one end to the arms 4 and 5 by rivets 11 or the like. The cuff components are constructed of relatively soft yieldable material such as plastic or cloth to conform to the limb configuration. The opposite ends of the cuff components 2 and 3 are fixed to relatively stiff bars 12 and 13 by rivets 11 or the like.

A cable 14 is releasably and adjustably secured with a cable clamp bolt 15 head on arm 4, passes through a guide 16 on bar 12, passes through guide 17 on arm 4 and is directed in a groove around cam 18 of lever mechanism 20. The cable is then secured to the lower end of the cam 18 by a cable clamp bolt head to provide a close fit of the upper limb engaging cuff component and to prevent loosening of the cuff component from the close fit position. The cam 18 is attached by bolts 20 or the like to lever 19 which is attached to end region 7 by bolts 20 or the like. The cam and lever can be constructed in various shapes and lengths to adjust the amount and rate of tightening of the cuff components.

A cable 21 is secured under cable clamp bolt 22 head on bar 13, passes through guide 23 on arm 5 and is directed through guide 24 on lever 25 attached to end region 6 by bolt 20a or the like. The cable is then releasably and adjustably secured under a cable clamp bolt 26 head on arm 4 to provide a close fit of the lower cuff component. A lever 28 is adjustably attached to end region 7 by a bolt 28a or the like and engages the cable 21 by a guide 29. The levers 25 and 28 can be adjusted such that the cuff component 3 is tightened from the close fit when the body part is moved away from a predetermined position relative to the other body part. In this instance in both flexion and extension of the thigh relative to the leg from the normal resting position.

In use, the cuff device is placed on the wearer's limb by situating the upper and lower arms 4 and 5 in the region of the knee or other articulation. The cuff components 2 and 3 are wrapped around the limbs and the cables 14 and 21 adjustably secured under the appropriate cable clamp bolt heads 15 and 26. The cuffs should have a close fit in the resting position for the articulation. The cable, lever and cam mechanisms are arranged and adjusted to tighten the cuff components when the body parts move in the direction of flexion and extension. However, numerous prophylactic and therapeutic conditions can be accomodated by various combinations and arrangements of the cables, levers and cams. One or both cuff components can be appropriately connected to the end regions to tighten in flexion or extension only or each in both directions from a predetermined position. One cuff device may serve to immobilize one arm and a tibia to prevent or restrain anterior and posterior movement of the tibia relative to the femur by arranging the mechanism to dynamically tighten on the limbs in both flexion and extension. As another example, the cuff can serve to protect the knee from lateral bending and rotation by tightening both cuffs in extension of the extremity. Further, the device can be arranged to first tighten the lower cuff component then the upper cuff component during the toe off and swing through phases of the wearer's gait to compress the limb to minimize stasis and improve venous return.

Referring to FIG. 4, there is provided in accordance with another embodiment of the present invention, a cuff assembly designated generally as 30. Except as hereinafter described, the cuff assembly 30 is substantially identical to the cuff assembly 1 and operates in the same manner for dynamically and momentarily tightening the cuff components on the body parts. For convenience, those features of the cuff assembly which are identical to those of the cuff assembly of FIGS. 1-3 are identified using the same numbers used in FIGS. 1-3. A pivot pin 8 is fixed in an opening in end region 6 and pivots freely in the opening in end region 7 as in the embodiment of FIGS. 1-3. A gear 31 is removably attached to the shaft of pivot pin 8 and rotates with pivot pin 8 relative to end region 7. A gear 32 is rotatably and removably attached to end region 7 by a bolt 33 or the like and has teeth that mesh with cooperating teeth on gear 31. Cable 14 passes from an upper limb engaging cuff component (not shown) and is secured in a groove in gear 32. Thus, hinging end regions 6 and 7 cause the cable 14 to wind and unwind on gear 32 tightening and loosening the cuff component. Using interchangeable gears of various sizes, the rate and amount of tightening and loosening can be adjusted for the individual requirement. A lower limb engaging cuff component (not shown) may be held tightly in a static manner using a conventional strap and a Velcro ® strip or additional cables, gears, cams and levers may be utilized to provide a dynamic fitting cuff assembly for the lower limb.

Referring to FIGS. 5-7 there is provided in accordance with still another embodiment of the present invention, a cuff assembly designated generally as 40. Except as hereinafter described, the cuff assembly 40 is substantially identical to the cuff assembly 1 and operates in the same manner for dynamically and momentarily tightening the cuff components on the body parts. Those features of the cuff assembly which are identical to those of the cuff assembly of FIGS. 1-3 are identified using the same numbers used in FIGS. 1-3. Arms 4 and 5 and end regions 6 and 7 operate in the same manner as the arms and end regions in FIGS. 1-3. A cuff component 42 is fixed at one end to the arm 4 by rivets 43 or the like. The cuff component 42 passes around the limb (not showm) passes through a loop 44 and is adjustably and releasably fixed to itself by a Velcro ® strip 45 or the like. The loop 44 is attached to a cable 46 which passes through guides 47 and 48 on arm 4 and is then directed around guide members 49 press fit in two of a series of holes 50 forming a cam plate in end region 7 and is releasably secured by a press fit hook 51 in one of the holes in end region 7 or a hole in pivot pin 8. Thus, hinging end regions 6 and 7 causes the cable 46 to tighten cuff component 42 in a direction generally transverse to the long axis of the body part when the arms are pivoted from the normal position. By guiding the cable around guide members selectively placed in holes in the end region, the normal position and rate and amount of tightening and loosening can be adjusted for the individual requirement. End region 7 includes a slot 52 to slidably engage a screw 53 attached in one of a series of threaded holes 54 in end region 6 to provide a stop to limit the extent of movement of hinging end regions 6 and 7. A cuff component complementary to cuff component 42 may be fixed to end region 5 or to an arm located on the opposite side of the body part and connected by an arm to cuff assembly 40.

Details have been disclosed to illustrate the invention in a preferred embodiment of which adaption and modification within the spirit and scope of the invention will occur to those skilled in the art. The scope of the invention is limited only by the following claims.

What is claimed is:

1. A dynamic support for first and second body parts which are articulated to each other comprising cuff components adapted to snugly engage the first and second body parts when the first and second body parts are in a resting position; the cuff components engaging the first and second body parts at locations spaced from the body area where the parts are articulated; arms attached to and extending from each of the cuff components and terminating in end regions, said end regions being movably attached to each other at a point adjacent the area where the body parts are articulated remote from the cuff components.

2. A dynamic support according to claim 1 wherein the tightening means comprises movable means.

3. A dynamic support according to claim 3 wherein the tightening means comprises a cable and gear assembly operatively coupling the cuff components with the arms.

4. A dynamic support according to claim 2 wherein the tightening means comprises means responsive to a predetermined movement from the resting position in more than one direction of one body part relative to the other body part.

5. A dynamic support according to claim 2 wherein the tightening means responsive to a predetermined relative movement is responsive to a predetermined flexion and extension of one body part relative to the other body part.

6. A dynamic support according to claim 2 wherein the tightening means responsive to a predetermined relative movement is responsive to a predetermined flexion of one body part relative to the other body part.

7. A dynamic support according to claim 2 wherein the tightening means responsive to a predetermined relative movement is responsive to a predetermined extension of one body part relative to the other body part.

8. A dynamic support according to claim 2 wherein the tightening means responsive to a predetermined relative movement is responsive to a predetermined sliding motion of one body part relative to the other body part.

9. A dynamic support according to claim 2 wherein the tightening means responsive to a predetermined relative movement is responsive to rotation of one body part relative to the other body part.

10. A dynamic support according to claim 2 wherein the tightening means responsive to a predetermined relative movement is responsive to a predetermined movement of the patient's leg relative to the patient's thigh.

11. A dynamic support according to claim 2 wherein the tightness increasing means temporarily increases the tightness of the fit between the cuff components and the patient's leg.

12. A dynamic support according to claim 2 wherein the tightness increasing means momentarily increases the tightness of the fit between the cuff components and the thigh.

13. A dynamic support according to claim 2 wherein the tightness increasing means increases the tightness of the fit in a direction generally transverse to a long axis of the body part.

14. A dynamic support according to claim 2 wherein the tightness increasing means adjusts the amount of tightening of at least one of the cuff components.

15. A dynamic support according to claim 3 wherein the tightening means comprises an adjustable cam and cable assembly operatively coupling the cuff components with the arms.

16. A dynamic support according to claim 15 wherein the cam and cable assembly comprises means for operatively coupling the cam and cable assembly to the end regions.

17. A dynamic support according to claim 16 wherein the cam and cable assembly further comprises a plate with multiple guide member holes.

18. A dynamic support according to claim 17 wherein the guide member holes releasably receive guide member pins.

19. A dynamic support according to claim 15 wherein the cam and cable assembly comprises means for adjusting the relative position of the arms when the first and second body parts are in their resting positions.

20. A dynamic support according to claim 15 wherein the cam and cable assembly comprises means for limiting the extent of movement of the arms.

21. A dynamic support according to claim 20 wherein the means for limiting the extent of movement of the arms comprises stop members on the arms.

22. A dynamic support according to claim 21 wherein the stop members comprise a slot end in one arm and and a screw member in the other arm.

23. A dynamic support according to claim 1 wherein the tightening means comprises a cable and lever assembly operatively coupling at least one of the cuff components with the arms attached thereto.

24. A dynamic support according to claim 23 wherein the tightening means further comprises a cam mechanism.

25. A support according to claim 1 wherein the body parts are movable in opposite directions from the resting position and said tightness increasing means temporarily increases the tightness with which at least one of the cuff components engages at least one of the body parts when said at least one of the body parts moves in either one of the opposite directions.

26. A dynamic support according to claim 1 wherein the cuff components comprise means for varying the tightness with which the cuff components engage the body parts when in the resting position.

27. A support according to claim 1 wherein the tightness increasing means temporarily increases the tightness with which at least one of the cuff components engages at least one of the body parts.

28. A dynamic support according to claim 1 wherein the arms comprise means for pivoting one arm relative to the other arm.

29. A dynamic support for first and second body parts of a patient articulated to each other by a joint permitting generally pivotal movements of the parts about a pivot axis with respect to each other from a resting position in which the parts are in an angular inclination relative to each other to a temporary position in which the parts are in a different angular inclination relative to each other, the support comprising: cuff means engaging the first and second body parts in their resting position with a predetermined tightness, the cuff means being constructed so as to have a component on each side and spaced from the joint when applied to the first and second body parts of the patient, arms connected with the cuff means and having end regions, said arms in substantial alignment with the longitudinal axes of the body parts; means pivotally securing the end regions of the arms to each other substantially coaxially with the pivot axis, tightening means attached to the cuff means and the end regions of the arms for increasing the tightness with which the cuff means engages at least one of the body parts when they are moved away from the resting position towards the temporary position.

30. A dynamic support according to claim 29 including means for varying the rate at which the tightening means increases the tightness with which the cuff means engages at least one of the body parts.

31. A dynamic support according to claim 30 wherein the means for varying the rate includes an adjustable cam assembly.

32. A dynamic support for first and second body parts which are articulated to each other comprising:
cuff components adapted to snugly engage the first and second body parts when the first and second parts are in a resting position;
the cuff components engaging the first and second body parts at locations spaced from the body area where the parts are articulated;
arms attached to and extending from each of the cuff components and terminating in end regions, said end regions being movably attached to each other at a point adjacent the area where the body parts are articulated remote from the cuff components;
tightening means attached to at least one of the cuff components and at least one arm; and
the tightening means including means responsive to a predetermined relative movement between the body parts in extension from the resting position for increasing the tightness with which at least one of the cuff components engages at least one of the body parts.

* * * * *

UNITED STATES PATENT AND TRADEMARK OFFICE
CERTIFICATE OF CORRECTION

PATENT NO. : 4,649,906
DATED : March 17, 1987
INVENTOR(S) : Richard G. Spademan

It is certified that error appears in the above-identified patent and that said Letters Patent is hereby corrected as shown below:

Claim 1, column 4, line 52, after "components", insert the following: --; tightening means attached to at least one of the cuff components and at least one end region; said tightening means including means responsive to a predetermined relative movement between the body parts in at least one direction away from the resting position for increasing the tightness with which at least one of the cuff components engages at least one of the body parts--.

Claim 3, line 3, delete "3" and substitute --2--.

Signed and Sealed this

Tenth Day of May, 1988

*Attest:*

DONALD J. QUIGG

*Attesting Officer*  *Commissioner of Patents and Trademarks*